United States Patent
Laskavy

(10) Patent No.: US 10,434,163 B2
(45) Date of Patent: Oct. 8, 2019

(54) REMEDY FOR BOVINE LEUKEMIA PROPHYLAXIS AND USE THEREOF

(71) Applicant: Andrei Valentinovich Ivlev, Mystischi (RU)

(72) Inventor: Vladislav Nikolaevich Laskavy, Saratov (RU)

(73) Assignee: Andrei Valentinovich Ivlev, Mytischi (RU)

( * ) Notice: Subject to any disclaimer, the term of this patent is extended or adjusted under 35 U.S.C. 154(b) by 0 days.

(21) Appl. No.: 15/836,943

(22) Filed: Dec. 11, 2017

(65) Prior Publication Data

US 2018/0169207 A1    Jun. 21, 2018

Related U.S. Application Data

(63) Continuation of application No. PCT/RU2017/000404, filed on Jun. 13, 2017.

(30) Foreign Application Priority Data

Nov. 22, 2016 (RU) ................................. 2016145862

(51) Int. Cl.
| | |
|---|---|
| *A61K 39/00* | (2006.01) |
| *A61K 39/04* | (2006.01) |
| *A61K 39/38* | (2006.01) |
| *A61P 35/02* | (2006.01) |
| *A61K 9/00* | (2006.01) |
| *C07K 14/35* | (2006.01) |

(52) U.S. Cl.
CPC ............. *A61K 39/04* (2013.01); *A61K 9/0019* (2013.01); *A61P 35/02* (2018.01); *C07K 14/35* (2013.01)

(58) Field of Classification Search
USPC ................................. 424/184.1, 234.1, 248.1
See application file for complete search history.

*Primary Examiner* — Rodney P Swartz

(57) ABSTRACT

The invention generally relates to the field of veterinary medicine and can be used for bovine leukemia prevention. The invention expands the range of means of the claimed application and provides lifelong resistance of animals to the leukemia virus.

The invention is aimed at solving the problem of expanding the range of preventive medications and forming new approaches to the problem of preventing bovine leukemia, which allow ensuring lifelong resistance of the animals to leukemia infection.

The technical result consists in the design of a remedy and use thereof for bovine leukemia prevention, which would allow providing a targeted immune response, efficiently and with minimal costs, by activating cellular immunity against bovine leukemia virus by increasing the number of killer cells.

The remedy for bovine leukemia prevention contains a water-soluble protein fraction with a molecular weight of 18-20 kDa, isolated from the tuberculosis mycobacterium destruction products, characterized by the presence of peaks at a wavelength of 214 nm in the UV region, a phosphate-buffered saline, an aqueous formaldehyde solution, and an isotonic sodium chloride solution.

The use consists in administering the said remedy to 1 to 9 days old calves with a single intramuscular injection at a dose of 4.0-6.0 ml per capita.

2 Claims, 1 Drawing Sheet

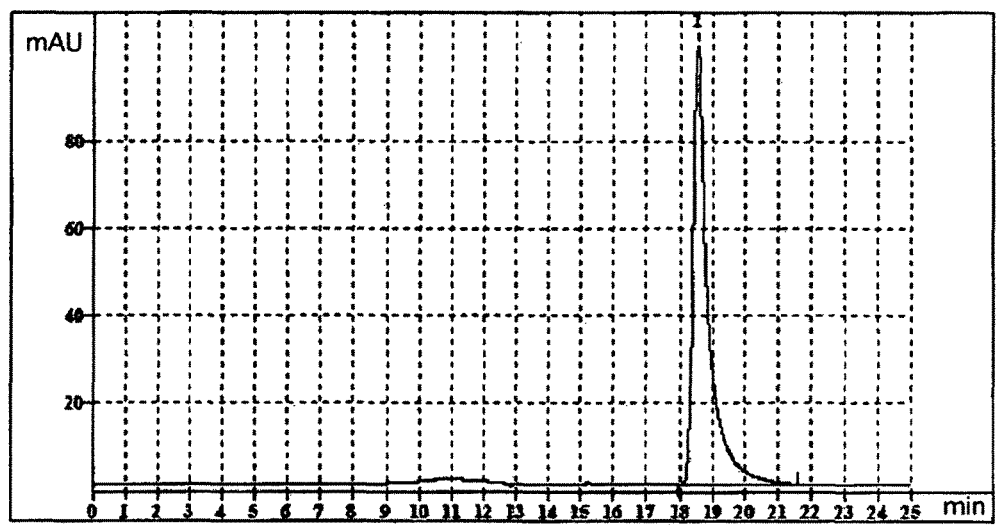

REMEDY FOR BOVINE LEUKEMIA PROPHYLAXIS AND USE THEREOF

CROSS-REFERENCE TO RELATED APPLICATIONS

The application is a continuation International Patent Application No. PCT/RU2017/000404, filed on Jun. 13, 2017, and claims priority to Russian Patent Application No. 2016145862, filed on Nov. 22, 2016, the entire specifications of both of which are expressly incorporated herein by reference.

FIELD OF THE INVENTION

The invention generally relates to the field of veterinary medicine and can be used to prevent bovine leukemia. The disclosure expands the range of means of the claimed application and provides the lifelong resistance of animals to bovine leukemia virus (BLV).

BACKGROUND OF THE INVENTION

Several remedies are hitherto known to prevent bovine leukemia and there are methods for preventing this disease using these medications.

An inactivated vaccine against bovine leukemia is known (see USSR author's certificate No 820,015, class A61K39/12, publ. Oct. 23, 1987) containing the protein fractions p25 and gP70 isolated from the peripheral blood leukemia cells of animals suffering from leukemia.

The obtained antigen-protein immunizing agent with Freund's complete adjuvant in a 1:1 ratio is administered to 1 to 3 month old calves. This immunization is carried out three times at intervals of 10-12 days.

Another inactivated vaccine against bovine leukemia is also disclosed (see RF patent No 2,202,367, IPC class A61K39/12, publ. Apr. 20, 2003), containing virus-containing leukocyte cells of the peripheral blood of animals. The immunization of animals is carried out subcutaneously three times with an interval of 10-14 days. Animals are vaccinated at the age of 2 months to 2 years.

These vaccines, however, have not found wide practical application due to the lack of means of immunological failure correction and the formation of low-titer antibodies.

Various remedies for bovine leukemia prevention are known as well.

In particular, the use of an amber biostimulator (see RF patent No 2,420,275, IPC class A61K31/194, publ. Jun. 10, 2011), polycarboxyethylene (see RF patent No 2,421,184, IPC class 2421184, publ. Jun. 20, 2011), metronidazole and norsulfazole or sulphadimezine (see RF patent No 2,300,883, IPC class A61K67/02, publ. Jun. 20, 2007), ligfol (see RU patent No 2,320,357, IPC class A61K36/00, publ. Mar. 27, 2008) etc. is known.

However, the influence of these preparations on the immune system at leukemia has not been studied and these remedies have found no practical application.

More particularly, metronidazole and sulfonamides have bactericidal rather than virucidal action, which does not allow them to render a specific effect on BLV. Ligfol is a hydrolyzate of natural lignin, humic substances being its active ingredient. Ligfol shows stress-corrector and adaptogenic actions, its injections are painful and cause long-term anxiety of animals. The effect of the amber biostimulator, which is a mixture of succinic acid and Dorogov's antiseptic stimulant (DAS), fraction No. 2, like that of any biologically active drug, has also been studied little and requires additional studies.

The closest to the present invention is the bovine leukemia prevention on the basis of tuberculosis toxoid (see RU patent No 2,396,978, IPC class A61K39/295, publ. Aug. 20, 2010). Tuberculosis toxoid is administered subcutaneously 20-30 days prior to vaccination with an inactivated vaccine against bovine leukemia. This tuberculosis toxoid is obtained (see, e.g., RU Patent No. 2,392,002, IPC class A61K39/00, publ. Jun. 20, 2010) by detoxification of tubercular exotoxins and endotoxins with two detoxifiers, namely, 0.2% formalin solution during 7-9 days at 42-45° C. and 0.5% aethonium solution during 7-9 days at 42-45° C.

However, this method for preventing bovine leukemia uses the mycobacteria destruction products in the whole, rather than the protein fraction isolated therefrom. The degradation product generally contains proteins, lipids, and polysaccharides. Lipids and polysaccharides increase the immunogenic load on the animal organism, change the homeostasis state and prevent a targeted immune response to mycobacteria proteins, which, in the end, reduces the efficiency of such preventive measures and does not ensure lifelong resistance of animals to the disease.

SUMMARY OF THE INVENTION

The invention is aimed at solving the problem of expanding the range of preventive means and forming new approaches to the problem of preventing bovine leukemia, which allow ensuring lifelong resistance of animals to leukemia infection.

The technical result achieved is the design of a remedy and use thereof for bovine leukemia prevention, which would allow providing a targeted immune response, with efficiency and minimal costs, by activating cellular immunity against bovine leukemia virus by increasing the number of killer cells.

To solve the task posed and to achieve this technical result, a group of claims is proposed, namely, a remedy for bovine leukemia prevention and a use thereof.

The technical result as to the remedy itself is achieved in that the remedy for preventing bovine leukemia, according to the disclosure, contains a water-soluble protein fraction with a molecular weight of 18-20 kDa isolated from the tuberculosis mycobacterium destruction products and characterized by the presence of peaks at a wavelength of 214 nm in the UV region, a phosphate-buffered saline, an aqueous formaldehyde solution, and an isotonic sodium chloride solution with the following component concentrations, wt %:

the water-soluble protein fraction with the molecular weight of 18-20 kD, isolated from the tuberculosis mycobacterium destruction products 0.05-0.125,

| | |
|---|---|
| the phosphate-buffered saline | 9.95-24.875 |
| the aqueous formaldehyde solution | 0.025-0.046, and |
| the isotonic sodium chloride solution | the rest. |

The said technical result, as to the use of this remedy, is achieved in that 1 to 9 day old calves are single injected intramuscularly, at a dose of 4.0-6.0 ml, the preparation containing the water-soluble protein fraction with the molecular weight of 18-20 kDa isolated from the tuberculosis mycobacterium destruction products and characterized by the presence of peaks at the wavelength of 214 nm in the UV region, the phosphate-buffered saline, the aqueous formaldehyde solution, and the isotonic sodium chloride solution with the following concentrations of these components, wt %:

the water-soluble protein fraction with the molecular weight of 18-20 kD, isolated from the tuberculosis mycobacterium destruction products 0.05-0.125,

| | |
|---|---|
| the phosphate-buffered saline | 9.95-24.875, |
| the aqueous formaldehyde solution | 0.025-0.046, and |
| the isotonic sodium chloride solution | the rest. |

The indicated features are significant and sufficient to obtain the claimed technical result.

The known sources of patent and scientific-technical information describe no preparations to prevent bovine leukemia, which would ensure lifelong resistance of animals to leukemia infection by activating their cellular immunity by increasing the number of killer cells. The mixture of the water-soluble protein fraction with the molecular weight of 18-20 kDa isolated from the tuberculosis mycobacterium destruction products in the phosphate-buffered saline with solutions of formaldehyde and sodium chloride provides activation of the killer defense system, namely, involvement of the T-lymphocyte ($Th_0$) subpopulation into immune response.

In the claimed remedy for bovine leukemia prevention, the mixture of a formaldehyde solution with an isotonic sodium chloride solution is used as a component providing stabilization of immune response at the killer system level rather than as a detoxifier.

Introduction of the only protein fraction or only formaldehyde does not give the desired result. Only the synergism of the components and their experimentally chosen concentrations make it possible to obtain a high effect of animals' resistance to leukemia infection by activating their killer system. Moreover, the formaldehyde concentration does not change the structure of the protein component of mycobacteria.

We have found a new, unobvious approach to solving the problem of preventing bovine leukemia by using a mixture of components (the protein fraction with a certain molecular weight extracted from the tuberculosis mycobacterium destruction products and a mixture of solutions of formaldehyde and sodium chloride) to increase the number of killer cells of the immune system.

Killer cells are known to inhibit the development of tumor cells (see, for example, RU patent No 2,443,411, IPC class A61K9/08, publ. Feb. 27, 2012, RU patent No 2,262,941, IPC class A61K35/16, publ. Oct. 27, 2005). However, they are used exclusively to treat the disease.

The use of the mechanism of increasing the number of killer cells of the immune system to prevent leukemia is hitherto unknown and has not been disclosed anywhere.

The use of any protein fraction isolated from the destruction products of tuberculosis mycobacterium to prevent leukemia is also unknown.

Administration of our remedy to calves up to 10 days of age (i.e., in the neonatal period) on the basis of a mixture of an isolated protein fraction with a formaldehyde solution for bovine leukemia prevention is also unknown.

Treatment of calves in their neonatal period by this remedy is explained by the fact that the humoral immunity is absent in such calves at birth, while the cellular one is already sufficiently developed. Cellular immunity activation at such an early age and, as a consequence, activation of the killer system of immunity, provides lifelong resistance of animals to leukemia infection.

Cytotoxic T-lymphocytes CD8 and inflammatory T-lymphocytes CD4 (Th1) are known to be responsible for cellular immunity, whilst T-helper lymphocytes CD4 (Th2) and B-lymphocytes are responsible for humoral immunity, respectively.

The present invention solves the problem of activating effective immunity against bovine leukemia by increasing cytotoxic lymphocytes (CD8) and inflammatory T-lymphocytes CD4 (Th1), decreasing T-helper lymphocytes CD4 (Th2), and increasing the number of the third subpopulation of Th lymphocytes (Th0).

Therefore, proper conditions in the organism of animals are created in advance for increasing the number of killer cells, which, being a barrier, inhibit the development of tumor cells. This mechanism allows the balance between cellular and humoral immunity to be preserved, which will be maintained throughout life.

The foregoing allows us to conclude on an inventive step criterion in the claimed invention.

BRIEF DESCRIPTION OF THE DRAWINGS

The disclosure is illustrated in FIG. 1, which shows the chromatogram of the protein fraction isolated from the destruction products of the causative agent of tuberculosis in cattle *M. bovis* (strain No. 8).

DETAILED DESCRIPTION

The remedy to prevent bovine leukemia is prepared as follows. As the destruction products of the causative agent of tuberculosis, PPD tuberculin for mammals is used, obtained from the strain *M. bovis* No. 8 and representing a clear liquid of light brown color.

To obtain the protein fraction, the liquid with the destruction products of the pathogen is precipitated with a saline solution (for example, ammonium sulfate) and centrifuged. The supernatant is then removed and the precipitate is redissolved in a saline buffer solution.

Dialysis is carried out, and the pH of the solution is adjusted to 7.0-7.4, after which the protein concentration is analyses by conventional methods, in particular, by the Lowry method.

The choice of such pH values of the solvent is explained by the corresponding value in the body cells. It is well known that pH in the body cells and the extracellular fluid is about 7.0 and 7.4, respectively.

The molecular weight of the protein was determined by high pressure liquid chromatography (HPLC), which was carried out, in particular, on a Stayer liquid chromatograph, using a spectrophotometric detector A214 (the wavelength 214 nm). A BioSep-SEC-S 2000 column (5 μm 145 A, 300×7.8 mm) was used for separation. 0.01 M phosphate-buffered saline was used as the eluent, the flow rate was 1 ml/min, or 0.01 M phosphate-buffered saline with 0.025% sodium azide solution (pH 6.8) and at a flow rate of 2 ml/min.

Bovine serum albumin with a molecular weight within 64-70 kDa, lactoferrin with a molecular weight of 75-80 kDa, and papain with a molecular weight of 20 kDa were used as standards.

Standard values were taken into account, such as the retention time of the sample on the column, or the retraction time (RT, min), the peak intensity by height (mAU), and the relative quantitative content of the substance, which was calculated as the percentage ratio of each peak to the total area of the peaks (A, %).

The major proteins in the fraction isolated from the destruction products of the causative agent of bovine tuberculosis *M. bovis* (strain No. 8) had molecular weights within 18-20 kDa (see FIG. 1).

Table 1 shows the result of chromatography of the composition based on the protein fraction isolated from the destruction products of the causative agent of bovine tuberculosis.

TABLE 1

| No. | Time, min | Height, mAU | Area, mAU · s | Resolution, n, n + 1 | A, % | Mol. weight, kDa |
|---|---|---|---|---|---|---|
| 1. | 18.54 | 100.18 | 3234.48 | 0.00 | 100 | 18-20 |

Next, the resulting protein fraction with the molecular weight of 18-20 kDa is mixed, in a buffer solution containing 4.8-5.2 mg/ml of the protein (i.e., 0.48-0.52%), with an isotonic sodium chloride solution, of a concentration within 0.85-0.95%.

To prepare a 50% solution of the protein fraction, 1 part of the buffer solution with the protein is taken and 1 part of the isotonic solution is added.

The composition of the resulting mixture is as follows:
the protein fraction—0.24-0.26%,
the phosphate-buffered saline—49.74-49.76%, and
the sodium chloride solution—the rest.

When preparing a 20% solution of the protein fraction, the composition of the resulting mixture will be as follows:
the protein fraction—0.096-0.104%,
the phosphate buffered saline—49.896-49.904%, and
the sodium chloride solution—the rest.

Next, a mixture of an aqueous formaldehyde solution with an isotonic sodium chloride solution is prepared.

To do this, 0.15-0.25 ml of a 36.5-37.5% medical solution of formic aldehyde (formaldehyde) is taken and added to 99.75-99.85 ml of an isotonic 0.85% (or 0.95%) solution of sodium chloride. The mixture of these solutions is stirred thoroughly.

The ratio of the components of the formaldehyde and isotonic sodium chloride solutions was selected experimentally.

When preparing the remedy from 37% formaldehyde solution, the final formaldehyde concentration in the resulting composition will be 0.055-0.099 wt %.

Then the resulting mixture of the solutions of the protein fraction in the buffer and isotonic solutions is mixed with the mixture of the formaldehyde and isotonic sodium chloride solutions.

Example 1. Preparation of the Remedy for Leukemia Prophylaxis 100 ml of PPD tuberculin for mammals, obtained from *M. bovis* strain No. 8 is taken. The protein fraction is prepared therefrom as follows.

42 g of ammonium sulfate is added to 100 ml of tuberculin to precipitate the protein, centrifuged at 4,500 rpm during 20 min. The supernatant is removed and the precipitate is redissolved in 1 ml of a 0.01 M phosphate-buffered saline. The system is dialyzed by means of a dialysis membrane with a pore diameter of 3,500 Da in a 0.01 M phosphate-buffered saline during 24 h, the pH of the solution is adjusted to 7.2-7.4, after which the protein concentration is determined by the Lowry method using a StatFax 3300 biochemical analyzer.

The concentration of the protein fraction from the destruction products of the causative agent of bovine tuberculosis was 5.0 mg/ml.

Analogously to Example 1, protein fractions from other batches of PPD tuberculin were obtained. The amount of protein everywhere varied from 4.8 to 5.2 mg/ml.

Next, the resulting protein fraction with the molecular weight of 18-20 kDa in the buffer solution containing 5 mg/ml protein (i.e. 0.5%) is mixed with the isotonic sodium chloride solution (0.85-0.95%).

A mixture of the aqueous formaldehyde solution and the isotonic sodium chloride solution is then prepared.

To do this, 0.2 ml of a 37% medical solution of formic aldehyde (formaldehyde) is taken and added to 99.8 ml of an isotonic (0.85%) sodium chloride solution. The mixture of these solutions is thoroughly stirred. The final formaldehyde concentration in the resulting composition will be 0.074 wt %.

The protein fraction in the phosphate-buffered saline is mixed with the mixture of solutions of formaldehyde and sodium chloride in equal proportions (1:1).

The contents of the components in the composition will be as follows, wt %:

| | |
|---|---|
| the water-soluble protein fraction with the molecular weight of 18-20 kD, isolated from the destruction products of mycobacterium of *M. bovis* strain No. 8 | 0.125 |
| the phosphate-buffered saline | 24.875 |
| the aqueous formaldehyde solution | 0.037, |
| the isotonic sodium chloride solution | the rest. |

Similarly, a remedy was prepared from protein fractions with protein contents of 0.48-0.52%.

Example 2. Substantiation of the Quantitative Content of Components in the Remedy 120 two to nine days old calves were used in our experiments, of which 108 were injected at doses of 4 to 6 ml to prevent leukemia with different quantitative contents of the components.

12 animals formed a reference group, which were injected pure saline in a dose of 5 ml per capita. The results are shown in Table 2.

TABLE 2

| Quantitative contents of components, wt % | | | | Dose of preparation, mL | Number of calves | Died | | Survived | |
|---|---|---|---|---|---|---|---|---|---|
| Protein fraction | Phosphate-buffered saline | Formal-dehyde solution | Isotonic NaCl solution | | | Nos | % | Nos | % |
| 0.05 | 9.95 | 0.037 | Rest to 100% | 4 | 12 | 0 | 0 | 12 | 100 |
|  |  |  |  | 5 | 12 | 1 | 8.3 | 11 | 91.7 |
|  |  |  |  | 6 | 12 | 3 | 25.0 | 9 | 75.0 |
| 0.075 | 14.925 | 0.037 | Rest to 100% | 4 | 12 | 2 | 16.7 | 10 | 83.3 |
|  |  |  |  | 5 | 12 | 0 | 0 | 12 | 100 |
|  |  |  |  | 6 | 12 | 2 | 16.7 | 10 | 83.3 |
| 0.125 | 24.875 | 0.037 | Rest to 100% | 4 | 12 | 0 | 0 | 12 | 100 |
|  |  |  |  | 5 | 12 | 0 | 0 | 12 | 100 |
|  |  |  |  | 6 | 12 | 1 | 8.3 | 11 | 91.7 |

4 animals of 12 were lost in the reference group, which was 33.3%.

Example 3

To substantiate the increased number of killer cells in the body of animals (heifers and cows), immunological studies of the blood of animals treated at the age of 2-9 days with our remedy to prevent bovine leukemia were carried out:
2.5 years old heifers, and
5 years old cows.
The results are shown in Table 3.

TABLE 3

Immunological indicators of 2.5 years old heifers and 5 years old cows

| Group | T-lymph. | Th-lymph. | Ts-lymph. | Th/Ts | T-active. | B-lymph. | Th0 |
|---|---|---|---|---|---|---|---|
| 2.5 years old HEIFERS | | | | | | | |
| Non-treated | 3343 ± 286.07 | 2054 ± 178.18 | 1295 ± 113.84 | 1.6 ± 0.07 | 1876 ± 159.95 | 459 ± 38.29 | 877 ± 97.93 |
| Treated | 3081 ± 249.9 | 1522 ± 133.1 | 1559 ± 132.3 | 1.0 ± 0.14 | 1631 ± 133.51 | 517 ± 39.5 | 1616 ± 242.7 |
| 5 years old COWS | | | | | | | |
| Non-treated | 2421.14 ± 279.34 | 1489.0 ± 157.85 | 931.29 ± 127.07 | 1.66 ± 0.11 | 1315.43 ± 154.77 | 288.43 ± 32.89 | 744.43 ± 110.62 |
| Treated | 4028.0 ± 586.89 | 2369.57 ± 345.5 | 1660.71 ± 241.39 | 1.43 ± 0.04 | 2167.86 ± 318.2 | 528.29 ± 68.81 | 1406.0 ± 203.93 |

From Table 3 it follows that the 2.5 years old heifers show a decreased ratio of T-helpers to T-suppressors (Th/Ts) and an increased number of the third subpopulation of T-lymphocytes (Th0).

In the 5 years old (experimental) cows, a significant increase in the contents of all lymphocyte fractions (T and B) was recorded while maintaining a high content of Th0 (killers).

The results of our serological tests for the presence of antibodies to BLV, carried out as the immunodiffusion reaction, in the heifers and cows aged 2.5 and 5 years, respectively, were negative.

Thus, the claimed remedy for bovine leukemia prevention, as well as the method of use thereof, ensures lifelong resistance of animals to leukemia infection by activating the cellular immunity against BLV by increasing the number of killer cells.

What is claimed is:

1. Remedy for bovine leukemia prevention characterized in that it contains:
   a water-soluble protein fraction with a molecular weight of 18-20 kDa, isolated from the destruction products of tuberculosis mycobacterium from the strain *M. bovis* No. 8 and characterized by the presence of peaks near the wavelength of 214 nm in the UV region,
   a phosphate-buffered saline,
   an aqueous formaldehyde solution, and
   an isotonic sodium chloride solution at the following ratio of the components, wt %:

| | |
|---|---|
| water-soluble protein fraction with the molecular weight of 18-20 kD, isolated from the destruction products of the tuberculosis mycobacterium from the strain *M. bovis* No. 8 | 0.05-0.125; |
| phosphate-buffered saline | 9.95-24.875; |
| formaldehyde aqueous solution of concentration within 36.5-37.5% | 0.025-0.046; |
| isotonic sodium chloride solution of concentration within 0.85-0.95% | the rest. |

2. Remedy for bovine leukemia prevention characterized in that it contains:
   a water-soluble protein fraction with a molecular weight of 18-20 kDa, isolated from the destruction products of the tuberculosis mycobacterium from the strain *M. bovis* No. 8 and characterized by the presence of peaks near the wavelength of 214 nm in the UV region,
   a phosphate-buffered saline, an aqueous formaldehyde solution, and
an isotonic sodium chloride solution at the following ratio of the components, wt %:

| | |
|---|---|
| water-soluble protein fraction with the molecular weight of 18-20 kD, isolated from the destruction products of the tuberculosis mycobacterium from the strain *M. bovis* No. 8 | 0.125; |
| phosphate-buffered saline | 24